United States Patent
Dietz et al.

(10) Patent No.: US 7,799,723 B2
(45) Date of Patent: Sep. 21, 2010

(54) METHOD FOR THE PRODUCTION OF MAGNESIUM ALKOXIDE GRANULES, AND USE THEREOF

(75) Inventors: Rainer Dietz, Egelsbach (DE); Ute Emmel, Frankfurt am Main (DE); Ulrich Wietelmann, Friedrichsforf (DE); Gerd Krämer, Vilbel (DE)

(73) Assignee: Chemetall GmbH, Frankfurt am Main (DE)

( * ) Notice: Subject to any disclaimer, the term of this patent is extended or adjusted under 35 U.S.C. 154(b) by 58 days.

(21) Appl. No.: 11/991,110

(22) PCT Filed: Sep. 1, 2006

(86) PCT No.: PCT/EP2006/065918

§ 371 (c)(1),
(2), (4) Date: Feb. 27, 2008

(87) PCT Pub. No.: WO2007/026017

PCT Pub. Date: Mar. 8, 2007

(65) Prior Publication Data
US 2009/0148702 A1 Jun. 11, 2009

(30) Foreign Application Priority Data
Sep. 1, 2005 (DE) .................. 10 2005 041 774

(51) Int. Cl.
*B01J 21/10* (2006.01)

(52) U.S. Cl. .................. 502/115; 502/103; 502/104
(58) Field of Classification Search .................. 502/102, 502/103, 104, 115; 423/155, 178, 161, 163
See application file for complete search history.

(56) References Cited

U.S. PATENT DOCUMENTS

| | | | | |
|---|---|---|---|---|
| 4,402,863 | A * | 9/1983 | Miyazaki et al. | 502/125 |
| 4,579,919 | A | 4/1986 | Staiger et al. | |
| 5,556,820 | A * | 9/1996 | Funabashi et al. | 502/111 |
| 6,297,188 | B1 | 10/2001 | Schork et al. | |
| 6,777,365 | B2 * | 8/2004 | Tanase et al. | 502/115 |
| 7,220,694 | B2 * | 5/2007 | Tanase et al. | 502/115 |
| 7,387,979 | B2 * | 6/2008 | Tanase et al. | 502/102 |
| 2003/0078457 | A1 | 4/2003 | Harthun et al. | |

FOREIGN PATENT DOCUMENTS

| | | |
|---|---|---|
| EP | 0 144 021 A1 | 6/1985 |
| EP | 0997451 A2 | 5/2000 |
| EP | 1 306 360 A2 | 5/2003 |

* cited by examiner

*Primary Examiner*—H. (Holly) T Le
(74) *Attorney, Agent, or Firm*—Fulbright & Jaworski L.L.P

(57) ABSTRACT

This invention relates to a process for preparing magnesium alkoxide granulates. The process includes the steps of reacting magnesium metal with at least one compound of formula $AlR_{3-n}Hal_n$ and an alcohol in a non-coordinating solvent. R is an alkyl or aryl radical, Hal is a halogen radical and n is in the range of between 0 and 2.

21 Claims, 1 Drawing Sheet

MG ETHYLATE FROM MG GRADE A, EXAMPLE 1

METHOD FOR THE PRODUCTION OF MAGNESIUM ALKOXIDE GRANULES, AND USE THEREOF

The present invention provides magnesium alkoxide granulates, a process for the preparation thereof and the use thereof.

Polyolefins are typically prepared from olefin monomers with the aid of an organometallic catalyst system of the Ziegler-Natta type. Ziegler-Natta catalysts generally comprise complexes formed from the halide of a transition metal, typically titanium, chromium or vanadium, and an aluminium alkyl. These complexes are conventionally heterogenized by application to an insoluble magnesium compound, for example a magnesium alkoxide, such as magnesium ethoxide.

An exchange process with the transition metal chloride proceeds on the surface of the magnesium alkoxide, for example:

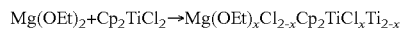

where x=0 or 1 and Cp=cyclopentadienyl (EP-A-1031580).

In the context of industrial usability, the magnesium alkoxide functioning as the support material and halogen acceptor must meet some physical framework conditions:
a) it should have the highest possible surface area, so that a correspondingly high catalyst activity can be achieved;
b) it should be dust-free and comprise readily flowable solid particles;
c) it should comprise particles as far as possible of similar size, that is to say it should have a narrow particle size distribution, so that a uniform polymerization is achieved, and
d) it should comprise as far as possible no impurities which interfere in the catalysis process, such as, for example, iodine.

Magnesium alkoxides of the general formula $Mg(OR)_2$ can be prepared by reaction of magnesium metal with the particular alcohol of the general formula ROH under reflux conditions. In order to accelerate the reaction, addition of a catalyst is required, typically iodine, which is added in amounts of about 1 mol %. Nevertheless, the reaction still takes a very long time. Thus, for example, for the preparation of magnesium ethoxide, about 11 hours (JP-A-03074341) or up to 24 hours (Tetrahedron Lett. 37, (1996) 5159-5160) are required if magnesium powder is employed.

During these long reaction times, the magnesium ethoxide particles formed as a rule disintegrate into a fine powder. At best spherical particles having very small diameters, for example 21.9 µm, can be produced (JP-A-03074341). In order to increase the rate of reaction and to be able to prepare a product with larger particles, for example larger than 500 µm, the reaction can be carried out in pure alcohol in an autoclave under elevated pressure and therefore at as elevated a temperature as possible (EP-A-997 451). This synthesis variant has the disadvantage that specific, expensive apparatuses are required. Furthermore, the magnesium ethoxide particles formed are saturated with excess alcoholate.

Since no protic substances, such as, for example, ethanol, may be present during the preparation and later use of the Ziegler-Natta catalysts, the coarse-grained product must be thoroughly washed and dried.

It is furthermore known to carry out the reaction of magnesium metal with ethanol in the presence of hydrocarbon solvents. U.S. Pat. No. 4,959,336 discloses reactions of magnesium powder in the presence of toluene, wherein a mixture of bromine and iron chloride is employed as the catalyst and the alcohol ethanol is already employed in the initial phase of the synthesis in excess, for example between 86% and 270%. Further considerable amounts of alcohol are added after a reaction time of some hours. The reaction is brought to completion by refluxing in the presence of titanium isopropoxide. Disadvantages of this process are the many stages and the long preparation times, for example some days under normal pressure or about one day or at least 6 hours for pressurized synthesis in an autoclave. Furthermore, the end product is contaminated with undesirable components from the catalyst mixture.

The object of the present invention is to overcome the disadvantages of the prior art.

According to the invention, the object is achieved by the features of the main claim. Preferred embodiments are to be found in the sub-claims.

In particular, an object of the present invention is to provide magnesium alkoxide granulates having an adjustable particle size and a process for the preparation of the magnesium alkoxide granulates according to the invention.

Further objects of the invention are to provide magnesium alkoxide granulates having an adjustable particle size, magnesium alkoxide granulates having a narrow particle size distribution and/or magnesium alkoxide granulates having a high internal surface area.

In this context, the objects are achieved according to the invention by a procedure in which magnesium metal is reacted with primary alcohols in aromatic hydrocarbon solvents at temperatures of between about room temperature and the boiling point of the particular alcohol, the alcohol being employed in a low excess, for example between 0.1 and 60%. The magnesium metal employed can be activated by known methods, such as, for example, iodine or bromine/iron chloride. Preferably, for activation the magnesium metal is pretreated in hydrocarbon suspension with small amounts, for example 0.001 to 2 mol %, preferably 0.1 to 1.5 mol % of an aluminium alkyl. In principle, however, higher amounts of aluminium alkyl, for example 10 or even more than 20 mol %, can also be employed. The increased addition of aluminium alkyl has the advantage that the viscosity of the alkoxide solutions is lowered. This makes these solutions easier to convey.

It has been found, surprisingly, that the magnesium alkoxide granulate is formed significantly faster by the process according to the invention than is the case according to the prior art, for example in pure alcohol or in a hydrocarbon/alcohol mixture with significantly excess alcohol. It has furthermore been found, surprisingly, that the particles formed which are prepared by the process according to the invention have an improved mechanical strength, that is to say they do not disintegrate during the synthesis process. The dust content, that is to say the content of particle size <0.2 mm in the end product, is therefore very low and a narrow particle size distribution is observed.

BRIEF DESCRIPTION OF THE DRAWINGS

FIGS. 1-3 show images of magnesium ethylate from examples 1-3; and

The particle diameter can be controlled by the choice of appropriate magnesium metal grades, as shown in Table 1:

TABLE 1

Magnesium grades

| Mg grade | Appearance | Particle dimensions Mg metal |
|---|---|---|
| A | fine filings | 1 mm wide, 3-6 mm long |
| B | granules | ø 0.5-1 mm |
| C | coarse filings | 3 mm wide, 3-10 mm long |

By reaction with primary alcohols, for example ethanol, under conditions according to the invention, granulates of high surface area having in some cases largely spherical shapes are formed.

TABLE 2

Product properties

Figure 1:
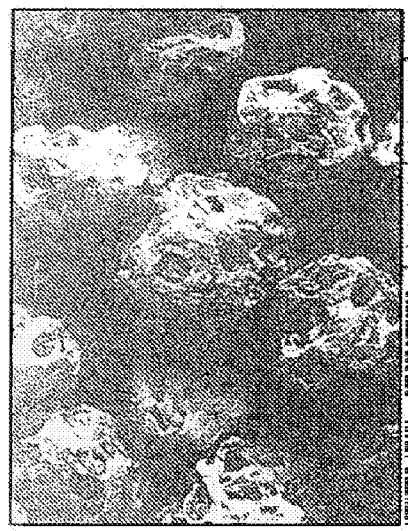
Figure 2:
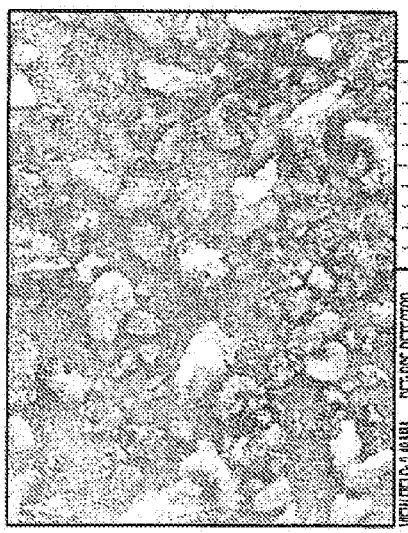
Figure 4:
FIG. 4 shows image of magnesium ethylate from comparison example 1.

| | Content in wt. % Sieve analysis (mm) | | | Image | |
|---|---|---|---|---|---|
| Mg employed | 0-0.5 | 0.5-1.6 | >1.6 | (FIG. 1) | Example no. |
| Grade A | 45 | 54 | 1 | 1 | 1 |
| Grade B | 0.5 | 99 | 0.5 | 2 | 2 |
| Grade C | 1 | 6 | 93 | 3 | 3 |
| Grade A | 92 | 7 | 1 | 4 | Comp. 1 |

The process according to the invention for the preparation of the magnesium alkoxide granulate is generally carried out as described below, without limiting the invention thereto:

An aromatic hydrocarbon solvent and magnesium metal, the aromatic hydrocarbon having 6 to 15 carbon atoms, are initially introduced into a stirred reactor which has been rendered inert, that is to say is dry and has been filled with an inert gas, for example nitrogen or argon.

Preferred solvents are: benzene, toluene, ethylbenzene, cumene or xylenes, either in the pure form or in a mixture of at least two of these solvents. The magnesium is employed in a commercially available form, that is to say in the form of powder, granules or filings. The particle size is chosen taking into consideration the desired particle diameter of the magnesium alkoxide. In general, magnesium particle sizes of from 0.3 to 5 mm are preferred; magnesium particle sizes of from 1 to 1.5 mm are particularly preferred. For the preparation of round, that is to say spherical, particles, a granulated magnesium is preferably used, for example grade B from Table 1. Granulated metal shapes which are already largely spherical have the advantage that the magnesium alkoxide granulate also results in a similar form. Furthermore, if such a granulate is employed, significantly less dust-like product is obtained, sometimes even none. This is a particular advantage for uses in catalysis, since in this case a granulate having a narrow particle-size distribution is required.

The reaction with an alcohol, for example primary alcohol, is inhibited because of the oxide layer which passivates the metal. An activation with a reagent which attacks the oxide layer and in this way exposes the active metal surface must therefore be carried out. This can be carried out by addition of known activating agents, that is to say iodine, bromine, iron chloride or the like. However, activation by aluminium compounds of the general formula $AlR_{3-n}Hal_n$, called activating agents in the following, is preferred, it being understood here and also in the following:

the radical R is an alkyl or aryl radical, preferably an alkyl radical, particularly preferably an alkyl radical having 1 to 8 C atoms;

the radical Hal is a halogen radical, preferably a chlorine, bromine or iodine radical;

n is a number, where $0 \leq n \leq 2$.

The use of trimethylaluminium (TMA), triethylaluminium (TEA), tributylaluminium (TBA), ethylaluminium dichloride (EADC) or diethylaluminium chloride (DEAC) or mixtures of two or more of these compounds is particularly preferred. These compounds are obtainable in commercial amounts as pure substances or as solutions in hydrocarbons.

The activating agent is preferably added to the suspension of the magnesium metal in an aromatic hydrocarbon, before the alcohol is added. The activating agent is added at temperatures of between 0 and 150° C., preferably between room temperature and 100° C. So that the activation can take place, it is necessary to maintain a certain contact time between the magnesium metal and the activating agent. The time required depends, for example, on the nature of the magnesium grade chosen, that is to say on the nature of the surface thereof. In general, contact times of between about one minute and some hours are sufficient. In order to facilitate the activation, it is appropriate in this context to stir the components or to homogenize them in another manner.

After activation has taken place, metering of the alcohol can be started. Depending on the batch size and other concomitant apparatus circumstances, metering is carried out over a period of from a few minutes to some hours. Typically, one to two hours are appropriate. In order to ensure a sufficiently high rate of reaction, primary alcohols are used. Methanol, ethanol or propanol are preferably employed, either in the pure form or in a mixture. However, the reaction is in principle also possible with secondary or tertiary alcohols, also in a mixture with one another or in a mixture with primary alcohols, in particular in a mixture with methanol and/or ethanol. The progress of the reaction can be monitored, for example, by observing the evolution of gas. The reaction is carried out in the temperature range between room temperature and about 150° C. Since the reaction is preferably conducted under normal pressure, the upper temperature limit is limited by the boiling point of the solvent, that is to say, for example, 110° C. in the case of toluene and 136° C. in the case of ethylbenzene.

The reaction is particularly preferably conducted at the boiling point. In this context, the suspension is preferably stirred cautiously, that is to say not very intensively. Too high an introduction of mechanical energy can lead to destruction of the magnesium alkoxide particles formed. The amount of aromatic hydrocarbon is chosen such that the magnesium metal and the magnesium alkoxide granulate form therefrom can be readily stirred. In general, the content of magnesium alkoxide in the finished reaction mixture is between 5 and 40 wt. %, preferably between 10 and 30 wt. %. The alcohol is employed with a slight excess, preferably an excess of between 0.1 and 60%, based on the amount necessary for complete conversion to the alkoxide. The amount of alcohol is particularly preferably between 101 and 120%, corresponding to an excess of 1 to 20%.

The contact time between the magnesium metal and the primary alcohol is chosen so that complete conversion of the metal is ensured, preferably 0.5 to 20 hours.

The mixture of product and hydrocarbon is worked up in a suitable form by methods according to the prior art. Preferably, the solvent is separated off by filtration or centrifugation and the solid magnesium alkoxide granulate is vacuum-dried. It is also possible for the volatile components, that is to say solvent and residual alcohol, to be removed by total evaporation. All these operations are carried out either in vacuo or under an inert gas without unnecessary introduction of mechanical energy, in order to avoid chemical or mechanical destruction of the product.

Finally, the end product can also be sieved, in order to separate off the dust content.

The average diameter $d_{50}$ of the grains of the magnesium alkoxide granulate is 0.3 to 5 mm, preferably 1 to 3 mm. The magnesium alkoxide granulate can be employed, for example, for the preparation of polymerization catalysts of the Ziegler-Natta type.

The invention provides, in detail:

a magnesium alkoxide granulate obtainable by reaction of magnesium with a compound or several compounds of the general formula $AlR_{3-n}Hal_n$ and an alcohol in a non-coordinating solvent;

a magnesium alkoxide granulate obtainable by reaction of magnesium with a compound or several compounds of the general formula $AlR_{3-n}Hal_n$ and an alcohol in a non-coordinating solvent, wherein the magnesium is initially introduced into the reaction vessel in a metallic form;

a magnesium alkoxide granulate obtainable by reaction of magnesium with a compound or several compounds of the general formula $AlR_{3-n}Hal_n$ and an alcohol in a non-coordinating solvent, wherein the magnesium is initially introduced into the reaction vessel in a granulated, spherical form;

a magnesium alkoxide granulate obtainable by reaction of magnesium with a compound or several compounds of the general formula $AlR_{3-n}Hal_n$ and an alcohol in a non-coordinating solvent, wherein the grain size of the magnesium is 0.3 to 5 mm, preferably 1 to 3 mm;

a magnesium alkoxide granulate obtainable by reaction of magnesium with a compound or several compounds of the general formula $AlR_{3-n}Hal_n$ and an alcohol in a non-coordinating solvent, wherein the alcohol is added after the compounds of the general formula $AlR_{3-n}Hal_n$;

a magnesium alkoxide granulate obtainable by reaction of magnesium with a compound or several compounds of the general formula $AlR_{3-n}Hal_n$ and a primary alcohol in a non-coordinating solvent, wherein the alcohol is a primary alcohol;

a magnesium alkoxide granulate obtainable by reaction of magnesium with a compound or several compounds of the general formula $AlR_{3-n}Hal_n$ and an alcohol in a non-coordinating solvent, wherein the alcohol is chosen from methanol, ethanol or propanol or mixtures of at least two of these alcohols;

a magnesium alkoxide granulate obtainable by reaction of magnesium with a compound or several compounds of the general formula $AlR_{3-n}Hal_n$ and an alcohol in a non-coordinating solvent, wherein the alcohol is ethanol;

a magnesium alkoxide granulate obtainable by reaction of magnesium with a compound or several compounds of the general formula $AlR_{3-n}Hal_n$ and an alcohol in a non-coordinating solvent, wherein the excess of the alcohol is between 0.1 and 60%, preferably between 1 and 20%;

a magnesium alkoxide granulate obtainable by reaction of magnesium with a compound or several compounds of the general formula $AlR_{3-n}Hal_n$ and an alcohol in a non-coordinating solvent, wherein the dust content in the product is not greater than 5%, preferably not greater than 3%, particularly preferably not greater than 2%;

a magnesium alkoxide granulate obtainable by reaction of magnesium with a compound or several compounds of the general formula $AlR_{3-n}Hal_n$ and an alcohol in a non-coordinating solvent, wherein the content of grains of the magnesium alkoxide granulate that are larger than 0.5 mm is greater than 20%, preferably greater than 50%, particularly preferably greater than 90% and very particularly preferably between 90 and 99%;

a magnesium alkoxide granulate obtainable by reaction of magnesium with a compound or several compounds of the general formula $AlR_{3-n}Hal_n$ and an alcohol in a non-coordinating solvent, wherein the average diameter $d_{50}$ of the grains of the magnesium alkoxide granulate is 0.3 to 5 mm, preferably 1 to 3 mm;

a magnesium alkoxide granulate obtainable by reaction of magnesium with a compound or several compounds of the general formula $AlR_{3-n}Hal_n$ and an alcohol in a non-coordinating solvent, wherein the average diameter $d_{50}$ of the grains of the magnesium alkoxide granulate is 0.3 to 5, preferably 1 to 3 mm;

a magnesium alkoxide granulate obtainable by reaction of magnesium with a compound or several compounds of the general formula $AlR_{3-n}Hal_n$ and an alcohol in a non-coordinating solvent, wherein the magnesium alkoxide granulate is present substantially in a spherical form;

a process for the preparation of a magnesium alkoxide granulate by reaction of magnesium with a compound or several compounds of the general formula $AlR_{3-n}Hal_n$ and an alcohol in a non-coordinating solvent;

a process for the preparation of a magnesium alkoxide granulate by reaction of magnesium with a compound or several compounds of the general formula $AlR_{3-n}Hal_n$ and an alcohol in a non-coordinating solvent, which comprises the following process steps:
  initial introduction of the solvent and the magnesium metal into a stirred reactor which has been filled with an inert gas;
  addition of one or more compounds of the general formula $AlR_{3-n}Hal_n$;
  addition of the alcohol;

a process for the preparation of a magnesium alkoxide granulate by reaction of magnesium with a compound or several compounds of the general formula $AlR_{3-n}Hal_n$ and an alcohol in a non-coordinating solvent, wherein the magnesium is initially introduced into the reaction vessel in a metallic form;

a process for the preparation of a magnesium alkoxide granulate by reaction of magnesium with a compound or several compounds of the general formula $AlR_{3-n}Hal_n$ and an alcohol in a non-coordinating solvent, wherein the magnesium is initially introduced into the reaction vessel in a granulated, spherical form;

a process for the preparation of a magnesium alkoxide granulate by reaction of magnesium with a compound or several compounds of the general formula $AlR_{3-n}Hal_n$ and an alcohol in a non-coordinating solvent, wherein the grain size of the magnesium is between 0.3 and 5 mm, preferably 1 to 3 mm;

a process for the preparation of a magnesium alkoxide granulate by reaction of magnesium with a compound or several compounds of the general formula $AlR_{3-n}Hal_n$ and an alcohol in a non-coordinating solvent, wherein the alcohol is added after the compounds of the general formula $AlR_{3-n}Hal_n$;

a process for the preparation of a magnesium alkoxide granulate by reaction of magnesium with a compound or several compounds of the general formula $AlR_{3-n}Hal_n$ and an alcohol in a non-coordinating solvent, wherein the alcohol is a primary alcohol;

a process for the preparation of a magnesium alkoxide granulate by reaction of magnesium with a compound or several compounds of the general formula $AlR_{3-n}Hal_n$ and an alcohol in a non-coordinating solvent, wherein the alcohol is chosen from methanol, ethanol or propanol or mixtures of at least two of these alcohols;

a process for the preparation of a magnesium alkoxide granulate obtainable by reaction of magnesium with a compound or several compounds of the general formula $AlR_{3-n}Hal_n$ and an alcohol in a non-coordinating solvent, wherein the alcohol is ethanol;

a process for the preparation of a magnesium alkoxide granulate by reaction of magnesium with a compound or several compounds of the general formula $AlR_{3-n}Hal_n$ and an alcohol in a non-coordinating solvent, wherein the excess of the alcohol is between 0.1 and 60%, preferably between 1 and 20%;

a process for the preparation of a magnesium alkoxide granulate by reaction of magnesium with a compound or several compounds of the general formula $AlR_{3-n}Hal_n$ and an alcohol in a non-coordinating solvent, wherein the solvent is chosen from benzene, toluene, ethylbenzene, cumene, xylenes or mixtures of at least two of these solvents;

a process for the preparation of a magnesium alkoxide granulate obtainable by reaction of magnesium with a compound or several compounds of the general formula $AlR_{3-n}Hal_n$ and an alcohol in a non-coordinating solvent, wherein the solvent is toluene;

a process for the preparation of a magnesium alkoxide granulate by reaction of magnesium with a compound or several compounds of the general formula $AlR_{3-n}Hal_n$ and an alcohol in a non-coordinating solvent, wherein the addition of the activating agent is carried out at temperatures of between 0 and 150° C., preferably between room temperature and 100° C.;

a process for the preparation of a magnesium alkoxide granulate by reaction of magnesium with a compound or several compounds of the general formula $AlR_{3-n}Hal_n$ and an alcohol in a non-coordinating solvent, wherein the period of time during which the alcohol is metered in is between 3 minutes and 6 hours, preferably between one and two hours;

a process for the preparation of a magnesium alkoxide granulate by reaction of magnesium with a compound or several compounds of the general formula $AlR_{3-n}Hal_n$ and an alcohol in a non-coordinating solvent, wherein the reaction of the magnesium with the alcohol is carried out at temperatures of between room temperature and 150° C., preferably between room temperature and the boiling point of the solvent;

use of the magnesium alkoxide granulate according to the invention for the preparation of polymerization catalysts of the Ziegler-Natta type.

The invention is explained in the following by examples, without limiting it thereto:

EXAMPLE 1

Preparation of a Magnesium Ethoxide Granulate by Reaction of Magnesium Fine Filings, Grade A, with Ethanol in a Toluene Suspension 77.3 g (3.180 mmol) of magnesium fine filings (NF2 from Minmet) in 1,400 g of toluene are initially introduced into a 3 l double-walled reactor which has been rendered inert and is provided with a propeller stirrer, dropping funnel and reflux condenser. The mixture is then heated to 50° C., with stirring, and 10 ml of a 25% strength solution of triethylaluminium in toluene are added. The mixture is stirred at the stated temperature for 30 minutes and metering in of anhydrous ethanol is then started. A total of 307 g of ethanol (6,660 mol, 4.7% excess) are added over a period of 1.5 hours. The reaction starts almost without delay, which can be seen from the increase in temperature and evolution of gas. The internal temperature is limited to 65° C. by counter-cooling. At the end of the addition, 55 l of gas (≈72% of th.) have evolved.

The jacket temperature is then increased to 90° C. After an after-reaction time of 100 minutes, the formation of gas stops. 75.8 l of gas (~99% of th.) in total have evolved.

The reaction mixture is drained off over a glass frit and the toluene phase is separated off. The residue on the filter is washed with hexane and initially predried at room temperature. For final drying, the solid is introduced into a 1 l round-bottomed flask and dried at 110° C. in vacuo.

338 g (93% of th.) of a granulated material having a dust content of 1.5% are obtained.

EXAMPLE 2

Preparation of a Magnesium Ethoxide Granulate by Reaction of Magnesium Granules, Grade B, with Ethanol in a Toluene Suspension The magnesium grade B is reacted with ethanol in toluene in the same apparatus as in Example 1. The reaction conditions and results are recorded in Tables 3 and 4.

EXAMPLE 3

Preparation of a Magnesium Ethoxide Granulate by Reaction of Magnesium Filings, Grade C, with Ethanol in a Toluene Suspension The magnesium grade C is reacted with ethanol in toluene in the same apparatus as in Example 1. The reaction conditions and results are recorded in Tables 3 and 4.

TABLE 3

Preparation of magnesium ethoxide granules

| Example | Magnesium Type | Amount (g) | Toluene (g) | Ethanol (g) | (% of th.) | TEA (g) | (mol %) |
|---|---|---|---|---|---|---|---|
| 1 | A | 77.3 | 1,400 | 307 | 105 | 2.5 | 0.7 |
| 2 | B | 80.5 | 1,550 | 355 | 116 | 1.1 | 0.3 |
| 3 | C | 65.3 | 1,630 | 267 | 108 | 2.3* | 1.2* |
| Comp. 1 | A | 76.0 | 0 | 2,050 | 712 | — | — |

*trimethylaluminium

TABLE 4

Preparation results

| Example | Reaction time (h) | Reaction temp. (° C.) | Amount of gas l | Amount of product (g) | Appearance | Dust content (%) |
|---|---|---|---|---|---|---|
| 1 | 3.2 | 50-90 | 75.8 | 338 | granules | 1.5 |
| 2 | 8 | 60-105 | 80.1 | 356 | granules | <1 |
| 3 | 4 | 90-108 | 64.3 | 281 | granules | 3 |
| Comp. 1 | 20 | 50-78 | 65.5 | 305 | powder with lumps | 72 |

In the process according to the invention, magnesium filings require about 3 to 4 hours for complete conversion into magnesium ethoxide. If more compact, granulated magnesium metal is employed, the reaction times are longer, as can be seen from Example 2. The dust content is below 1%.

COMPARISON EXAMPLE 1

Preparation of Magnesium Ethoxide by Reaction of Magnesium in Anhydrous Ethanol 76 g of magnesium fine filings are suspended in 2.05 kg of anhydrous ethanol (Karl Fischer water content: 36 ppm) in the apparatus from Example 1 and the jacket temperature is raised to 90° C. in the course of 20 minutes, so that the contents of the reactor boil. After 70 minutes in total, just about 20 l of gas (approx. 26% of th.) have evolved. Thereafter, the gas formation rate decreases sharply. Within a further 4 hours of boiling under reflux, only 21 l of gas are liberated. Thereafter, 0.8 g of iodine and, after a further hour, 1.8 g of iron chloride are added. The gas formation rate thereafter increased only briefly. After refluxing for 15 and 20 hours in total, 57.6 and, respectively, 65.5 l of gas have formed (approx. 77 and, respectively, 87% of th.).

The grey-white suspension is filtered and vacuum drying is carried out at 110° C. The finished product predominantly comprises a fine powder having a very high dust content. In addition to lumps, it also contains about 10% of unreacted metallic magnesium.

The invention claimed is:

1. A process comprising preparing a granulate comprising magnesium alkoxide by reacting magnesium metal with at least one compound of formula $AlR_{3-n}Hal_n$ and an alcohol in a non-coordinating solvent, wherein R is an alkyl or aryl radical, Hal is a halogen radical, and n is a number, wherein $0 \leq n \leq 2$.

2. The process according to claim 1, comprising the steps of:

initially introducing the solvent and the magnesium metal into a stirred reactor which has been filled with an inert gas;

adding the at least one compound of formula $AlR_{3-n}Hal_n$; and adding the alcohol, wherein R is an alkyl or aryl radical, Hal is a halogen radical, and n is a number, wherein $0 \leq n \leq 2$.

3. The process according to claim 1, wherein the magnesium metal is initially introduced into a reaction vessel in which the reaction takes place in a metallic form.

4. The process according to claim 3, wherein the grain size of the magnesium is between 0.3 and 5 mm.

5. The process according to claim 3, wherein the magnesium is initially introduced into the reaction vessel in a granulated, spherical form.

6. The process according to claim 1, wherein the alcohol is added after the compounds of the general formula $AlR_{3-n}Hal_n$, wherein R is an alkyl or aryl radical, Hal is a halogen radical, and n is a number, wherein $0 \leq n \leq 2$.

7. The process according to claim 1, wherein the alcohol is a primary alcohol.

8. The process according to claim 1, wherein the alcohol is at least one of methanol, ethanol or propanol.

9. The process according to claim 8, wherein the alcohol is ethanol.

10. The process according to claim 1, wherein an excess of the alcohol is provided between 0.1 and 60%.

11. The process according to claim 1, wherein the solvent is at least one of benzene, toluene, ethylbenzene, cumene or a xylene.

12. The process according to claim 11, wherein the solvent is toluene.

13. The process according to claim 1, wherein an activating agent is added at a temperature of between 0 and 150° C.

14. The process according to claim 1, wherein the alcohol is metered in over a time period of between 3 minutes and 6 hours.

15. The process according to claim 1, wherein the reaction of the magnesium with the alcohol is carried out at temperature of between room temperature and 150° C.

16. The process according to claim 1, wherein the reaction of the magnesium with the alcohol is carried out at temperature of between room temperature and the boiling point of the solvent.

17. The process according to claim 1, wherein the average diameter $d_{50}$ of the granulate is from 1 to 3 mm.

18. The process according to claim 1, wherein the content of the magnesium alkoxide granulate which are larger than 0.5 mm is greater than 50%.

19. The process according to claim 1, wherein the content of the magnesium alkoxide granulate which are larger than 0.5 mm is greater than 90%.

20. The process according to claim 1, wherein the content of the magnesium alkoxide granulate larger than 0.5 mm is between 90 and 99%.

21. A method comprising preparing a Ziegler-Natta type catalyst with the granulate prepared by the process of claim 1.

* * * * *